US00PP24335P3

(12) United States Plant Patent
Harris

(10) Patent No.: US PP24,335 P3
(45) Date of Patent: Mar. 25, 2014

(54) AZALEA PLANT NAMED 'MNIHAR025'

(50) Latin Name: ***Rhododendron* sp.**
Varietal Denomination: MNIHAR025

(76) Inventors: James O. Harris, Lawrenceville, GA (US); Ella Ruth Harris, legal representative, Lawrenceville, GA (US)

( * ) Notice: Subject to any disclaimer, the term of this patent is extended or adjusted under 35 U.S.C. 154(b) by 45 days.

(21) Appl. No.: 13/573,112

(22) Filed: Aug. 22, 2012

(65) Prior Publication Data

US 2014/0059728 P1 Feb. 27, 2014

(51) Int. Cl.
*A01H 5/00* (2006.01)

(52) U.S. Cl.
USPC ..... Plt./240

(58) Field of Classification Search
USPC ..... Plt./240
See application file for complete search history.

*Primary Examiner* — Annette Para
(74) *Attorney, Agent, or Firm* — Jondle Plant Sciences Division of Swanson & Bratschun, L.L.C.

(57) ABSTRACT

A new and distinct variety of azalea plant with spring and fall blooming, attractive, showy, single red flowers, easily propagated by semi-hardwood cuttings in late spring through summer, moderate growth rate under normal fertilization and moisture conditions; compact, broadly-globose and freely-branching growth habit, grows well in containers, thrives in shade or sun and is hardy to Zone 7, is disclosed.

2 Drawing Sheets

Genus and species: *Rhododendron* sp.
Variety denomination: 'MNIHAR025'.

BACKGROUND OF THE NEW PLANT

The present invention is a new and distinct variety of evergreen azalea of the genus *Rhododendron*. This new azalea, hereinafter referred to as 'MNIHAR025', originated from a planned cross hybridization in 2002 between the female azalea plant 'Conleb' (U.S. Plant Pat. No. 10,581) and the male azalea plant 'Jay Valentine' (unpatented) in a controlled environment in Lawrenceville, Ga. The present invention has both spring and fall blooming. 'MNIHAR025' has a compact, broadly globose freely branching growth habit, and cold hardiness.

The new plant was first propagated via semi-hardwood cuttings in 2005 in Dearing, Ga. and has been asexually reproduced repeatedly by semi-hardwood cuttings in Dearing, Ga. for over 7 years, four generations. 'MNIHAR025' has been found to retain its distinctive characteristics through successive asexual propagations via semi-hardwood cuttings.

Plant Breeder's Rights for this variety have not been applied for. 'MNIHAR025' has not been made publicly available or sold more than one year prior to the filing date of this application.

SUMMARY OF THE INVENTION

The following are the most outstanding and distinguishing characteristics of this new cultivar when grown under normal horticultural practices in Dearing, Ga.

1. Spring and fall blooming;
2. Attractive, showy, red colored flowers;
3. Numerous single flowers;
4. Easily propagated by semi-hardwood cuttings in late spring through summer;
5. Moderate growth rate under normal fertilization and moisture conditions;

6. Compact, broadly globose freely branching growth habit;
7. Grows well in containers;
8. Thrives in shade or sun; and
9. Hardy to Zone 7.

DESCRIPTION OF THE PHOTOGRAPHS

This new azalea hybrid is illustrated by the accompanying photographs. The colors shown are as true as can be reasonably obtained by conventional photographic means. The photographs are of four-year-old plants grown in filtered shade and full sun in 2010 and 2011 in Dearing, Ga.

DETAILED BOTANICAL DESCRIPTION OF THE NEW PLANT

Figure 1:
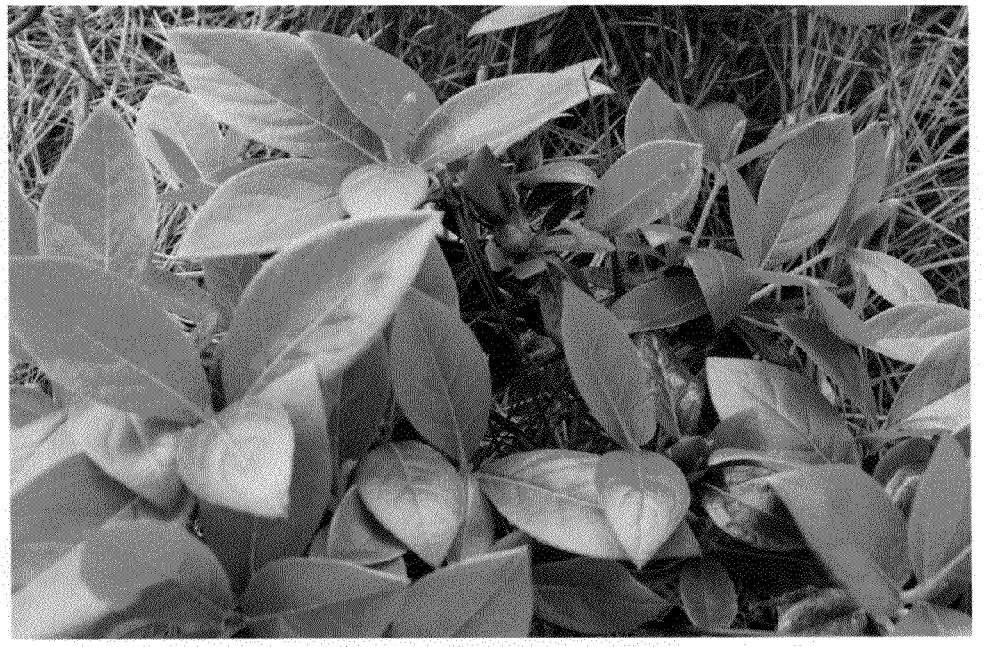
FIG. 1 shows a close-up of flower buds and immature foliage.
Figure 2:
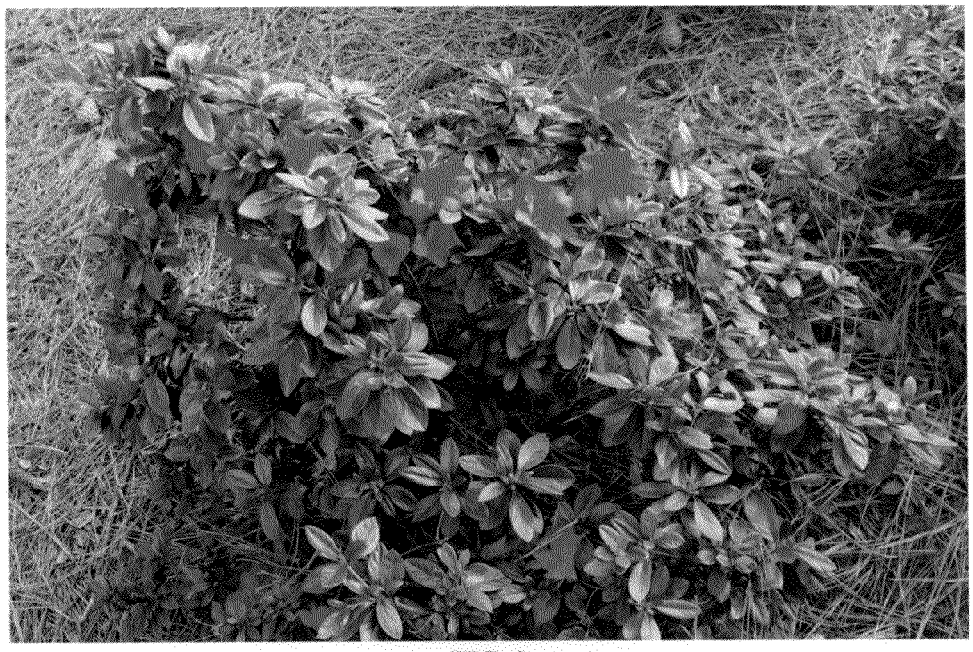
FIG. 2 shows mature foliage and growth habit and fall flowering.
Figure 3:
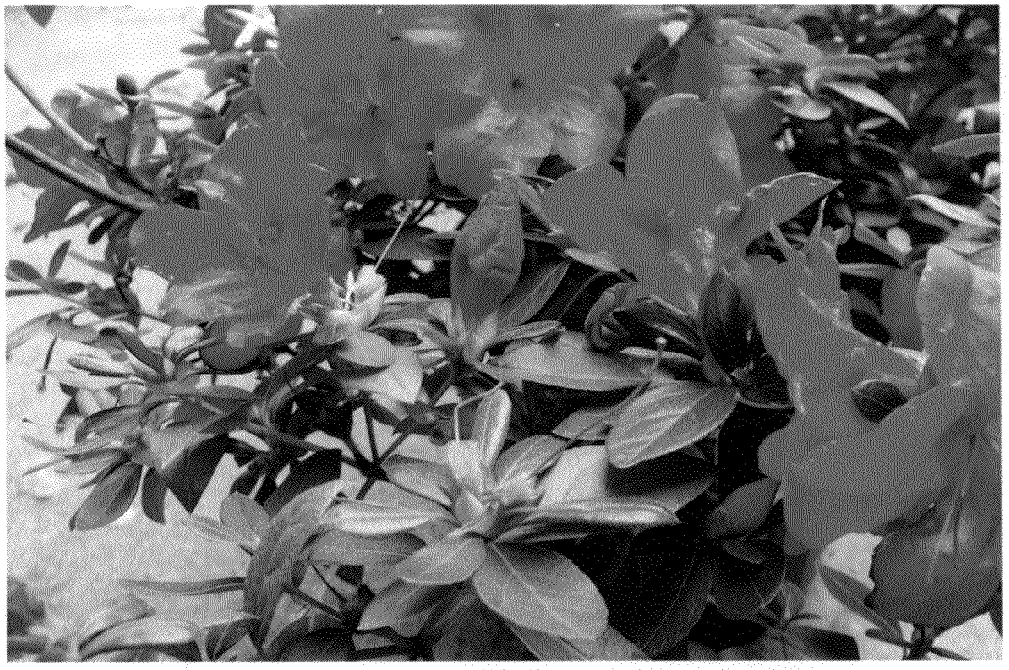
FIG. 3 shows a close-up of flower buds and mature foliage.
Figure 4:
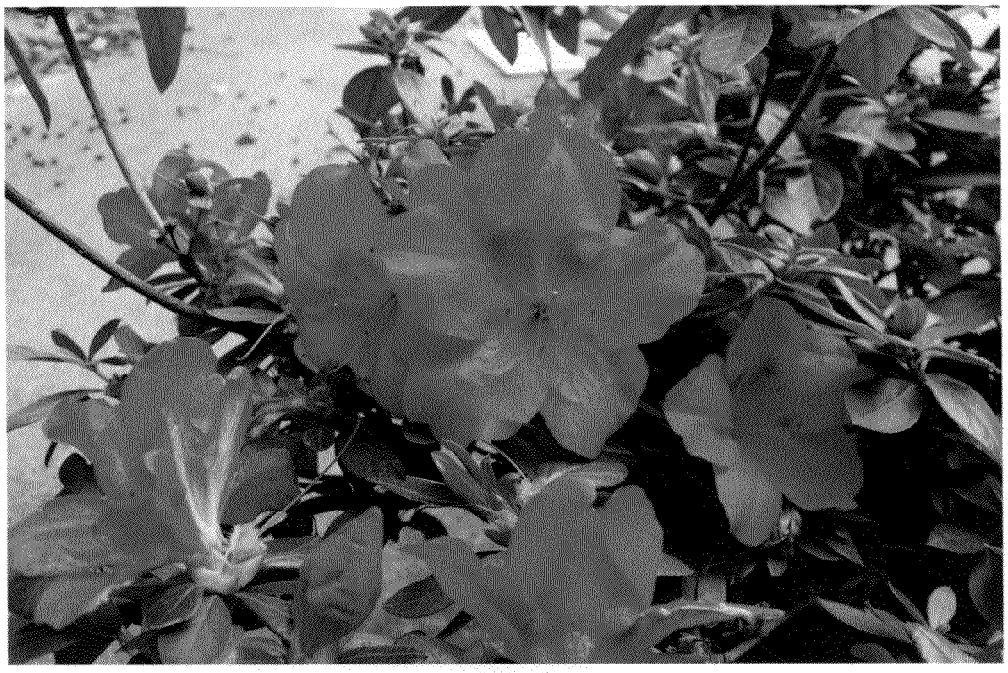
FIG. 4 shows a close-up of flower size, form, and color.

The following is a detailed description of the new azalea variety based on observations made of two and three-year-old plants grown in trade and three-gallon containers according to wholesale commercial production conditions, under full-sun and in an evaluation bed under semi-shade conditions in Dearing, Ga. in the spring, summer, and fall seasons of 2008, 2009, 2010, 2011, and 2012. The colors of the various plant parts are detailed with reference to The Royal Horticultural Society Colour Chart (2001).

Classification:

*Family*.—Ericaceae.
*Species*.—*Rhododendron* sp.
*Common name*.—Azalea.
*Denomination*.—'MNIHAR025'.

Parentage:

*Female parent*.—The azalea plant 'Conleb' (U.S. Plant Pat. No. 10,581).

*Male parent*.—The azalea plant 'Jay Valentine' (unpatented).

Plant:

*Form*.—Compact, broadly globose.

*Texture*.—Medium.

*Height* (*at maturity*).—60.96 cm to 76.2 cm.

*Width* (*at maturity*).—91.44 cm to 121.92 cm.

*Growth habit*.—Freely branching; compact, broadly globose.

*Growth rate*.—Moderate growth rate under normal fertilization and moisture conditions. In a period of 5 years from a rooted cutting the plant reaches a height of 39.0 cm and a spread of 69.0 cm. The growth rate is normally averages about 8.0 cm per year; the plant reaches a height of 60.96 cm to 76.2 cm at maturity while maintaining a compact broadly globose habit due to the abundant deliquescent branch development.

*Spring growth*.—The date of initial spring growth is March 26, followed by continuous growth through fall.

*Life cycle*.—Perennial and evergreen.

Leaves:

*Arrangement*.—Alternate, simple, pubescent, and evergreen.

*Shape*.—Elliptical to oblanceolate.

*Apex*.—Mucronate.

*Base*.—Attenuate.

*Margin*.—Entire.

*Length*.—4.5 cm.

*Width*.—2.3 cm.

*Venation pattern*.—Pinnate, the mid-veins and laterals are impressed on the upper surface and the prominent on the lower surface. Midvein Color (both upper and lower surfaces): RHS 144B (yellow-green).

*Immature leaf*.—Upper surface: Color: Semi-glossy, RHS 144A (yellow-green). Pubescence: Strigose. Color: RHS N155A (white) and RHS 161B (greyed-yellow). Lower surface: Color: Semi-glossy, RHS 144B (yellow-green). Pubescence: Strigose. Color: RHS N155A (white) and RHS 161D (greyed-yellow).

*Mature leaf*.—Upper surface: Color: Semi-glossy, RHS 139A (green). Pubescence: Strigose. Color: RHS 164D (greyed-orange). Lower surface: Color: Semi-glossy, RHS 146B (yellow-green). Pubescence: Strigose. Color: RHS 164C (greyed-orange).

*Petiole*.—Length: 0.6 cm. Diameter: 0.1 cm by 0.15 cm. Pubescence: Strigose. Length: 0.16 cm. Color: Immature: RHS N155A (white) and RHS 161B (greyed-yellow). Mature: RHS 161B (greyed-yellow). Color: Immature (both upper and lower surfaces): RHS 144B (yellow-green). Mature (both upper and lower surfaces): RHS 144B (yellow-green).

Stems:

*Form*.—Branched at terminal buds with some from auxiliary buds at leaf nodes.

*Young stems* (*actively growing, less than one year old*).—Color: RHS 144B (yellow-green) maturing to N199C (grey-brown). Pubescence: Strigose, decreasing in amount with age. Color: Begins RHS N155A (white) maturing to RHS 165C (greyed-orange). Length of fully elongated flush: 3.8 cm on average. Diameter: 0.2 cm.

*Mature stems* (*one year old and older*).—Color: RHS N199B (greyed-brown), RHS 200C (brown). Pubescence: None observed. Length: 9.5 cm on average for full year's growth. Diameter: 0.25 cm in second year. Pith: Solid and uniform. Internode length: Average 1.1 cm on actively growing vegetative stems.

Flower buds:

*Arrangement and form* (*at terminal end*).—Borne in groups of two or three, sheathed by zero, one, two, or three modified leaf bracts.

*Bracts*.—Length: 1.9 cm. Width: 0.4 cm. Color: RHS 139A (green).

*Shape*.—Ovate.

*Apex*.—Acute.

*Base*.—Rounded.

*Length* (*at tight bud*).—1.2 cm.

*Diameter* (*at tight bud*).—0.6 cm.

*Scales*.—Color: Immature: RHS 144D (yellow-green). Mature: RHS 144B (yellow-green). Length: 1.1 cm. Diameter: 0.8 cm. Texture: Matte, strigose pubescence. Pubescence color: RHS 165B (greyed-orange).

*Pedicel*.—Length: 0.8 cm at point bud begins to open. Diameter: 0.2 cm. Texture: Pubescent, sericeous and strigose pubescence. Pubescence color: RHS N155A (white) with some RHS 164D (greyed-orange). Color: RHS 145A (yellow-green) with areas of RHS N34A (orange-red).

Calyx:

*Diameter*.—0.7 cm from sepal apex to sepal apex.

*Texture*.—Pubescent, villous and some sericeous pubescence. Pubescence color: RHS N155A (white).

*Color*.—RHS 144B (yellow-green).

*Sepals*.—Length: 0.4 cm. Diameter: 0.3 cm. Quantity: 5.

Flowers:

*Type*.—Perfect, single flowers.

*Shape*.—Open funnel-shaped.

*Flowering habit and period*.—Borne on the current season's growth; three weeks in April in Dearing, Ga.; flowering resumes late July and continues until frost which can be as late as November or December.

*Lastingness of flowers on the plant*.—4 to 6 days in the sun; 4 to 7 days in the shade.

*Fragrance*.—Absent.

*Persistence*.—Self-cleaning.

*Diameter*.—7.6 cm.

*Depth*.—3.4 cm.

*Petals*.—Quantity per flower and arrangement: Five imbricate petals that are fused at the base and remain fused up to 1.9 cm from the base of petals without spots, 2.6 cm from the base of petals with spots. Shape: Obovate. Apex: Rounded. Base: Fused. Margin: Entire. Texture (both upper and lower surfaces): Glabrous. Length (petals without spots): 5.2 cm. Width (petals without spots): 2.8 cm. Length (petals with spots): 5.4 cm. Width (petals with spots): 2.6 cm. Color: Upper surface: RHS 42A (red); spots RHS 60A (red-purple). Lower surface: RHS 47A (red): spots are not visible.

Reproductive parts:

*Pistil*.—Quantity and form: Single, non-petaloid. Length: 3.7 cm. Diameter: 0.05 cm.

*Stigma*.—Color: RHS 53A (red). Diameter: 0.15 cm.

*Style color*.—RHS 46A (red).

*Ovary*.—Pilose pubescence RHS N155A (white) with 5 locules.

*Ovary color*.—RHS 141A (green).

*Stamens*.—Quantity: 5 per flower; non-petaloid, rarely petaloid. Filament length: Average 3.2 cm. Width: 0.05 cm for non-petaloid, 1.8 cm for petaloid. Color: RHS 50A (red).

*Anther*.—Length: 0.3 cm. Width: 0.1 cm. Color: RHS 187A (greyed-purple). Pollen: Abundant. Color: RHS 155A (white).

Fruit and seed: Observed.

*Maturity*.—The capsule matures in about 6 months in Dearing, Ga. and the fruit set is low and contains about 100 to 200 non-winged seeds.

*Capsules*.—Length: 1.1 cm. Width: 0.6 cm. Color: RHS 146A (yellow-green).

CULTURE

'MNIHAR025' grows well in a wide range of conditions and tolerates sun to shade. 'MNIHAR025' prefers moist, well-drained soil that is rich in organic matter and responds well to mulching and medium applications of fertilizer. 'MNIHAR025' does best in soil with a pH of 5.0 to 5.5 and is propagated with semi-hardwood cuttings in late spring through the summer. 'MNIHAR025' roots in five to six weeks with a high percentage of rooting (80% plus). Tissue culture is also an effective means of propagation for 'MNIHAR025'.

DISEASES AND INSECTS

Susceptible to lace bugs, root weevils, and spider mites. Fungal and bacterial pathogens have not been observed, but no resistance testing has been performed.

COMPARISON WITH PARENTAL AND COMMERCIAL VARIEITES

In Table 1, 'MNIHAR025' is compared to parental varieties 'Conleb' (U.S. Plant Pat. No. 10,581) and 'Jay Valentine' (unpatented).

TABLE 1

| Characteristic | 'MNIHAR025' | 'Conleb' | 'Jay Valentine' |
|---|---|---|---|
| Plant Height (Mature) | 60.96 cm to 76.2 cm | 121.92 cm to 152.4 cm | 121.92 cm |
| Flower Diameter | 7.6 cm | 6.5 cm | 6.25 cm to 7.62 cm |
| Flower Form | Single | Single to semi-double | Single |
| Flower Color | Red | Red | Deep Red |
| Bloom Period | April and late July until frost | April and late July until frost | April |
| Hardy Zone | 7 | 7 | 7 |
| Stamen Number | 5 | 0 to 9 | 5 |
| Stamen Type | Non-petaloid, rarely petaloid | Petaloid and non-petaloid | Non-petaloid |

When 'MNIHAR025' is compared to the commercial variety 'Roblen' (U.S. Plant Pat. No. 16,248), 'MNIHAR025' has a compact broadly globose growth habit with a height of 39.0 cm and a spread of 69.0 cm in 5 years, while 'Roblen' has a height of 91.44 cm and a spread of 60.96 cm in 6 years. Additionally, 'MNIHAR025' has single flowers with petals colored RHS 42A (red) on the upper and lower surfaces, whereas 'Roblen' has semi-double flowers with petals colored RHS 44C (red).

I claim:

1. A new variety of azalea plant named 'MNIHAR025' as herein shown and Described.

* * * * *